(12) United States Patent
Southern et al.

(10) Patent No.: US 6,770,751 B2
(45) Date of Patent: Aug. 3, 2004

(54) METHOD FOR ANALYSING A POLYNUCLEOTIDE CONTAINING A VARIABLE SEQUENCE AND A SET OR ARRAY OF OLIGONUCLEOTIDES THEREFOR

(75) Inventors: Edwin Mellor Southern, Kidlington (GB); Clare Elizabeth Pritchard, Abingdon (GB); Stephen Charles Case-Green, Oxford (GB)

(73) Assignee: Oxford Gene Technology IP Limited, Oxfordshire (GB)

( * ) Notice: Subject to any disclaimer, the term of this patent is extended or adjusted under 35 U.S.C. 154(b) by 186 days.

(21) Appl. No.: 09/934,604

(22) Filed: Aug. 23, 2001

(65) Prior Publication Data

US 2002/0106665 A1 Aug. 8, 2002

Related U.S. Application Data

(62) Division of application No. 09/502,778, filed on Feb. 11, 2000, now Pat. No. 6,307,039, which is a division of application No. 08/930,798, filed as application No. PCT/GB96/00848 on Apr. 9, 1996, now Pat. No. 6,150,095.

(30) Foreign Application Priority Data

Apr. 9, 1996 (GB) .............................................. 9507238

(51) Int. Cl.[7] .............................................. C07H 21/04
(52) U.S. Cl. ................................................... 536/24.3
(58) Field of Search ................................ 536/24.3, 25.3

(56) References Cited

U.S. PATENT DOCUMENTS

| | | | |
|---|---|---|---|
| 4,797,355 A | 1/1989 | Stabinsky | 435/6 |
| 4,851,331 A | 7/1989 | Vary et al. | 435/6 |

(List continued on next page.)

FOREIGN PATENT DOCUMENTS

| | | |
|---|---|---|
| EP | 0 185 494 | 6/1986 |
| EP | 0 246 864 | 11/1987 |
| EP | 0 552 545 A1 | 7/1993 |
| EP | 0 721 016 | 7/1996 |
| WO | 89/10977 | 11/1989 |
| WO | 92/15712 | 9/1992 |

(List continued on next page.)

OTHER PUBLICATIONS

J. Prosser, "Detecting Single–Base Mutations", Trends in Biotechnology, vol. 11, pp. 238–246, Jun. 1993.

C. Pritchard et al., "Spatially Addressable Ligation Assays: Application of Oligonucleotide Arrays to DNA Fingerprinting", Innovation Perspect Solid Phase Synth. Comb. Libr. Collect Pap. Int. Symp. 4th, pp. 499–502, 1996.

T. Nikiforov et al., "Genetic Bit Analysis: A Solid Phase Method for Typing Single Nucletoide Polymorphisms", Nucleic Acids Research, vol. 22, No. 20, pp. 4167–4175, 1994.

S. Case–Green et al., "Studies on the Base Pairing Properties of Deoxyinosine by Solid Phase Hybridisation to Oligonucleotides", Nucleic Acids Research, vol. 22, No. 2, pp. 131–136, 1994.

J. Shumaker et al., "Mutation Detection by Solid Phase Primer Extension", Human Mutation, vol. 7, pp. 346–354, 1996.

*Primary Examiner*—Kenneth R. Horlick
(74) *Attorney, Agent, or Firm*—Wenderoth, Lind & Ponack, L.L.P.

(57) ABSTRACT

A method of analysing a polynucleotide target involves incubating the target with an oligonucleotide probe, generally an array of immobilized oligonucleotide probes, to form a duplex, and using ligase or polymerase to extend one chain of the duplex. A point mutation or variable number tandem repeat section may be analyzed. Arrays of immobilized oligonucleotides are provided for use in the method.

15 Claims, 7 Drawing Sheets

U.S. PATENT DOCUMENTS

| | | | |
|---|---|---|---|
| 5,348,853 A | 9/1994 | Wang et al. | 435/6 |
| 5,679,524 A | 10/1997 | Nikiforov et al. | 435/6 |
| 5,700,637 A | 12/1997 | Southern | 435/6 |
| 5,723,320 A | 3/1998 | Dehlinger | 435/91.1 |
| 5,759,779 A | 6/1998 | Dehlinger | 435/6 |
| 5,800,994 A | 9/1998 | Martinelli et al. | 435/6 |
| 5,858,659 A | 1/1999 | Sapolsky et al. | 435/6 |
| 5,981,176 A | 11/1999 | Wallace | 435/6 |
| 6,004,744 A | 12/1999 | Goelet et al. | 435/5 |

FOREIGN PATENT DOCUMENTS

| | | |
|---|---|---|
| WO | 93/25563 | 12/1993 |
| WO | 94/11530 | 5/1994 |
| WO | 95/00669 | 1/1995 |
| WO | 95/04160 | 2/1995 |
| WO | 95/09248 | 4/1995 |
| WO | 95/21271 | 8/1995 |
| WO | 95/27078 | 10/1995 |

Detection of point mutation by single base extension

Detection of point mutation by hybridisation to ASOs and chain extension

A. Detection of point mutation by tag ligation to ASOs

B. Detection of point mutation by ligation to library of differentially tagged ASOs Analysis of VNTRs by ligation of tag to allelic variants A. Target repeats equal probe B. Target repeats more than probe C. Target repeats less than probe Analysis of VNTRs by ligation of tag to allelic variants A. Target repeats equal probe B. Target repeats more than probe C. Target repeats less than probe Measurement of VNTRs by labelled chain extension Number of repeats proportional to */6

Analysis of VNTRs by ligation of tag followed by chain extension

A. Target repeats equal probe

B. Target repeats more than probe

C. Target repeats less than probe

METHOD FOR ANALYSING A POLYNUCLEOTIDE CONTAINING A VARIABLE SEQUENCE AND A SET OR ARRAY OF OLIGONUCLEOTIDES THEREFOR

This application is a divisional of Ser. No. 09/502,778 filed Feb. 11, 2000, U.S. Pat. No. 6,307,039, which is a divisional of Ser. No. 08/930,798 filed Oct. 6, 1997, U.S. Pat. No. 6,150,095 which is a PCT/GB96/00848, filed Apr. 9, 1996.

BACKGROUND OF THE INVENTION

Detection of variation in DNA sequences forms the basis of many applications in modern genetic analysis: it is used in linkage analysis to track disease genes in human pedigrees or economically important traits in animal and plant breeding programmes; it forms the basis of fingerprinting methods used in forensic and paternity testing [Krawczak and Schmidtke, 1994]; it is used to discover mutations in biologically and clinically important genes [Cooper and Krawczak, 1989]. The importance of DNA polymorphism is underlined by the large number of methods that have been developed to detect and measure it [Cotton, 1993]. Most of these methods depend on one of two analytical procedures, gel electrophoresis or molecular reassociation, to detect sequence variation. Each of these powerful procedures has its drawbacks. Gel electrophoresis has very high resolving power, and is especially useful for the detection of variation in the mini- and microsatellite markers that are used in linkage analysis and fingerprinting; it is also the method used to analyse the variation found in the triplet repeats that cause a number of mutations now known to be the cause of around ten genetic disorders in humans [Willems, 1994]. Despite its great success and widespread use, gel electrophoresis has proved difficult to automate: even the systems which automate data collection require manual gel preparation; and as samples are loaded by hand, it is easy to confuse samples. The continuous reading electrophoresis machines are expensive, and manual analysis is technically demanding, so that its use is confined to specialised laboratories which have a high throughput. Furthermore, difficulties in measuring fragment size preclude rigorous statistical analysis of the results.

By contrast, oligonucleotide hybridisation lends itself to automation and to quantitative analysis [Southern et al., 1992], but it is not well suited to the analysis of variation in the number of repeats in the micro- and minisatellites, as the small fractional change in the number of repeats produces a barely detectable change in signal strength; and of course it would not be possible to distinguish two alleles in the same sample as each would contribute to a single intensity measurement. Thus, many different combinations of alleles would produce the same signal. Present hybridisation methods are much better suited to analysing variation in the DNA due to point mutation-base substitution deletions and insertions, for which it is possible to design allele specific oligonucleotides (ASOs) that recognise both the wild type and the mutant sequences [Conner et al., 1983]. Thus it is possible in principle, in a relatively simple test, to detect all possible genotypes. However, a problem that arises in practice in the use of oligonucleotide hybridisation is that in some cases the extent of reassociation is barely affected by a mismatched base pair.

BRIEF SUMMARY OF THE INVENTION

The invention describes a general approach which can be applied to all forms of variation commonly used as DNA markers for genetic analysis. It combines sequence-specific hybridisation to oligonucleotides, which in the preferred embodiment are tethered to a solid support, with enzymatic reactions which enhance the discrimination between matching and non-matching duplexes, and at the same time provide a way of attaching a label to indicate when or which reaction has taken place. Two enzymatic reactions, chain extension by DNA dependent DNA polymerases and DNA strand-joining by DNA ligases, are dependent on perfect matching of sequences at or around the point of extension or joining. As we shall show, there are several ways in which these enzymes can be used with sequence-specific oligonucleotides to detect variation in target sequences.

In all cases, the sequence to be analysed, the target sequence, will be available as a nucleic acid molecule, and may be a DNA molecule produced, for example, by the polymerase chain reaction. However, the methods are not confined to analysis of DNA produced in this way. In all applications, the target sequence is first captured by hybridisation to oligonucleotides which are preferably tethered to a solid support; for example, the oligonucleotides may be synthesised in situ as described [Maskos and Southern, 1992]; or they may be presynthesised and then coupled to the surface [Khrapko et al, 1991].

In one aspect of the invention the novelty arises from the exploitation of enzymes in combination with substrates or primers tethered to solid supports. A further novelty exploits the observation that DNA ligases and polymerases can be used to distinguish sequence variants which differ in the number of units of a tandemly repeating sequence. This observation is surprising, as tandemly repeated sequences can form duplex in any register, thus in principle, length variants can form duplexes which match at the ends even when the two strands contain different numbers of repeat units. Although we demonstrate the application of this method in conjunction with tethered oligonucleotides, it should be evident that this reaction could be used to analyse VNTR (variable number tandem repeat) sequences in the liquid phase followed by some other method of analysis, such as gel electrophoresis.

In one aspect the invention provides a method of analysis which comprises: providing a polynucleotide target including a nucleotide at a specified position, and an oligonucleotide probe, tethered to a support, said probe being complementary to the target and terminating at or close to the said specified position; and performing the steps:
a) incubating the target with the probe to form a duplex,
b) incubating the duplex under ligation conditions with a labelled oligonucleotide complementary to the target,
c) and monitoring ligation in b) as an indication of a point mutation at the specified position in the target.

In another aspect the invention provides a method of analysis which comprises: providing a polynucleotide target having a variable number tandem repeat section and a flanking section, and an oligonucleotide probe having a section complementary to the repeat section and a flanking section of the target; and performing the steps:
a) incubating the target with the probe to form a duplex,
b) incubating the duplex with a labelled oligonucleotide and/or at least one labelled nucleotide under chain extension conditions,
c) and monitoring chain extension as an indication of the length of the variable number repeat section of the target.

A polynucleotide target is provided, in solution when the probe is tethered to a support, and may be DNA or RNA. This polynucleotide target is caused to hybridise with an oligonucleotide probe. The term oligonucleotide is used here, as common terminology far the primers and substrates commonly utilised by polymerase and ligase enzymes. However, the term is used in a broad sense to cover any substance that serves as a substrate for the enzymes, including single stranded chains of short or moderate length composed of the residues of nucleotides or of nucleotide analogues, and also longer chains that would ordinarily be referred to as polynucleotides.

The probe may be tethered to a support, preferably by a covalent linkage and preferably through a 5' or 3' terminal nucleotide residue. An array of oligonucleotide probes may be tethered at spaced locations, for example on a derivatised glass surface or the surface of a silicon microchip, or alternatively on individual beads.

In another aspect the invention provides an array of oligonucleotides, for analysing a polynucleotide target containing a variable sequence, in which each component oligonucleotide i) comprises a sequence complementary to the target including an expected variant of the target, and ii) is tethered to a solid support in a chemical orientation which a) permits duplex formation with the target, and b) permits chain extension only when the sequence of the oligonucleotide matches the variable sequence of the target.

In another aspect the invention provides a set or array of oligonucleotides, for analysing a polynucleotide target containing a variable number tandem repeat sequence, in which each component oligonucleotide i) comprises a sequence complementary to a part of the target-immediately adjacent the repeat sequence, ii) comprises a sequence complementary to the repeat sequence of the target and containing a number of repeats expected in the target, and iii) is configured in a way that a) permits duplex formation with the target, and b) permits chain extension only when the number of repeats in the oligonucleotide equals or is less than the number of repeats in the target.

In another aspect the invention provides an array of oligonucleotides in which different oligonucleotides occupy different locations and each oligonucleotide has a 3' nucleotide residue through which it is covalently tethered to a support and a 5' nucleotide residue which is phosphorylated.

The invention also provides a method of making an array of different oligonucleotides tethered to different locations of a support, which method comprises the steps of: providing a first intermediate oligonucleotide tethered to the support and a second intermediate oligonucleotide in solution, and a third oligonucleotide that is complementary to both the first and second intermediate oligonucleotides, forming a duplex of the third oligonucleotide with the first and second intermediate oligonucleotides, and ligating the first intermediate oligonucleotide with the second intermediate oligonucleotide; and repeating the steps with oligonucleotides tethered to different locations of the support.

BRIEF DESCRIPTION OF THE DRAWINGS

Reference is directed to the accompanying drawings in which each of FIGS. 1 to 6 is a series of diagrams illustrating a method according to the invention.

DETAILED DESCRIPTION OF THE INVENTION

Detection of Point Mutation

I. Single Base-specific Extension of Tethered Primers

Figure 1:
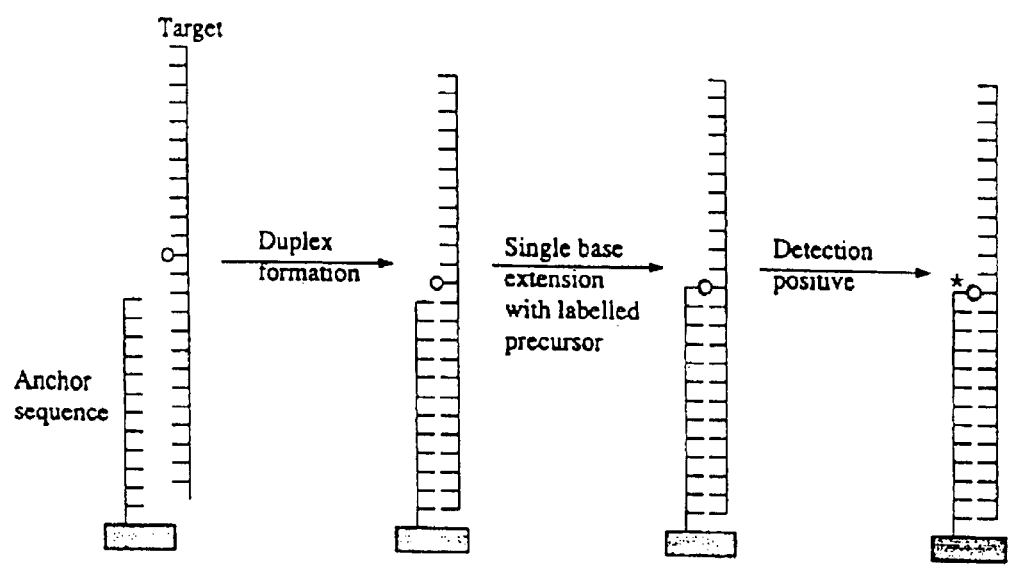
FIG. 1 shows detection of point mutation by single base extension.
Figure 1:
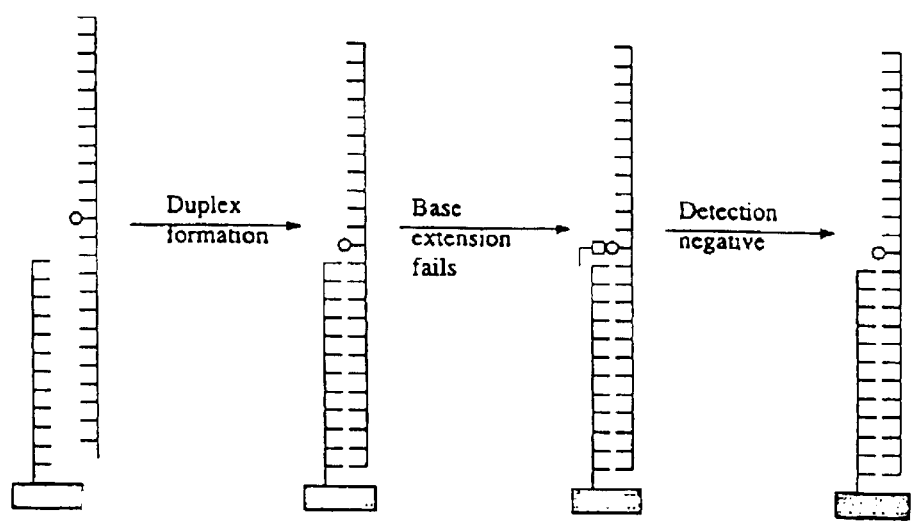

In this application, the tethered oligonucleotide terminates at a position one base before the variable base in the target sequence (FIG. 1). A nucleotide precursor triphosphate or dideoxyribonucleotide triphosphate, labelled, for example with a fluorescent tag, is added in the presence of a nucleic acid synthesising enzyme which requires a specific template in order to incorporate the complementary base. In the case of DNA polymerase, the labelled base will be incorporated from a deoxyribonucleotide precursor only if the precursor base is complementary to the base in the target sequence. Thus, mutants will give a negative result.

II. Chain Extension from Tethered ASOs

Figure 2:
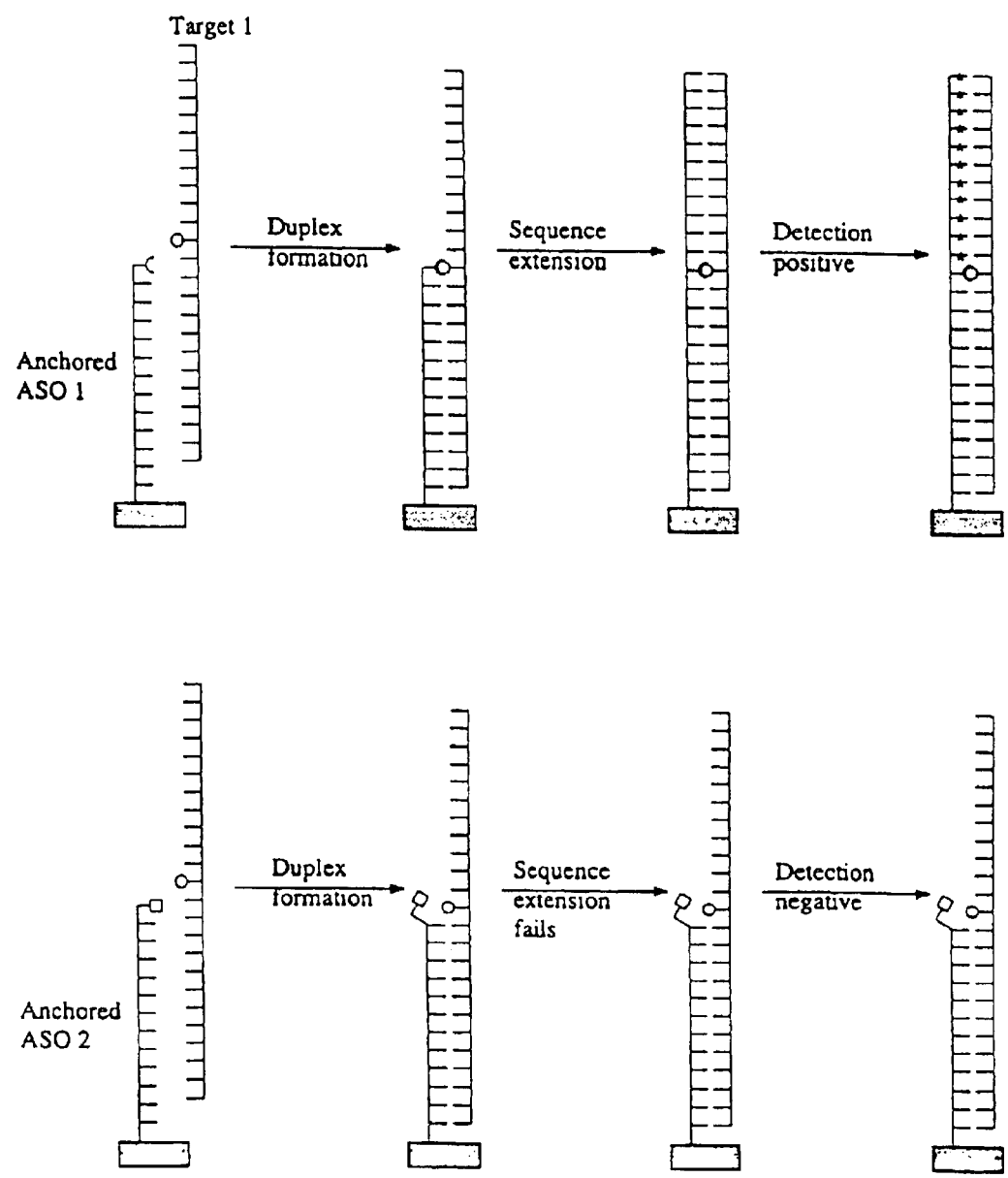
FIG. 2 shows detection of point mutation by hybridisation to allele specific oligonucleotides and chain extension.

In this case, the tethered oligonucleotide terminates in a base which is complementary to the variable base in the target sequence. Labelled precursor nucleoside triphosphates and polymerase are added. Polymerisation takes place only if the last base of the primer is complementary to the variable base in the target (FIG. 2). Thus, mutants will give a negative result.

III. Ligation of Tag Sequences to Tethered ASOs

Figure 3:
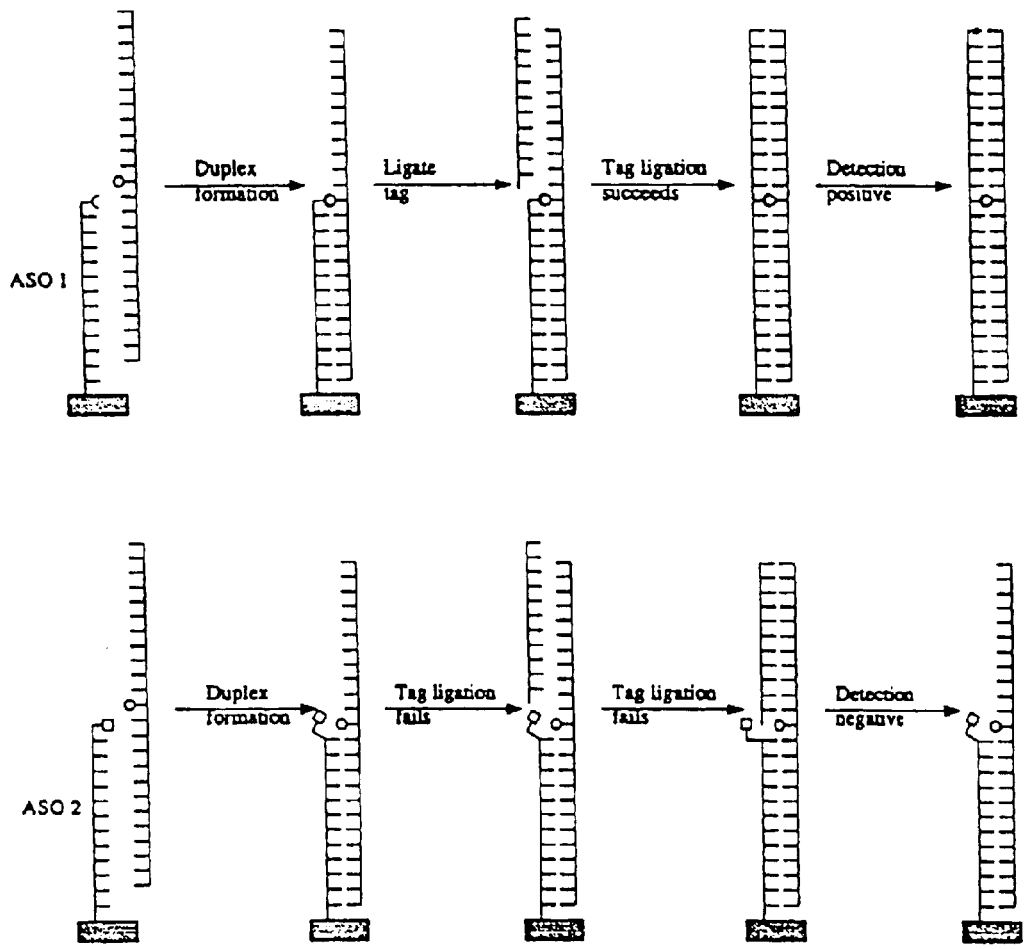
FIG. 3A shows detection of point mutation by tag ligation to allele specific oligonucleotides.
FIG. 3B shows detection of point mutation by ligation to library of differentially tagged allele specific oligonucleotides.
Figure 3:
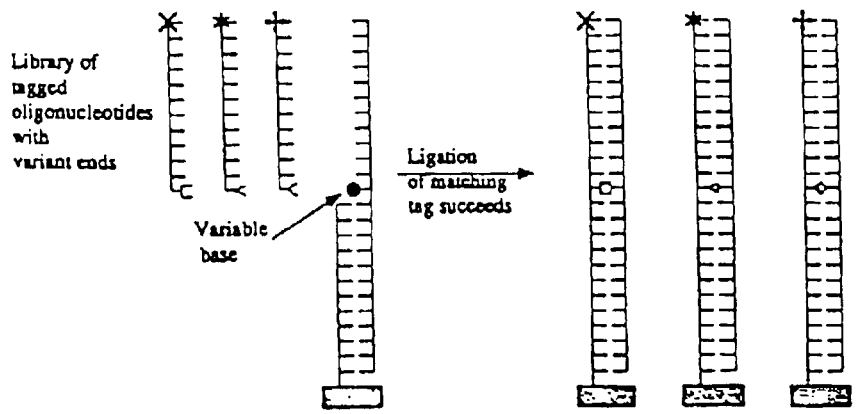

In this method, the tethered oligonucleotide may end at the variable position in the target sequence, or it may end close to this position. In either case, hybridisation of the target to the tethered ASOs will produce a substrate for ligating a tag oligonucleotide only if the bases at the join are well matched (FIG. 3a). Thus, mutants which are close enough to the joining position to prevent ligation will give a negative result. Alternatively, the tethered oligonucleotide may terminate at the base before the variable position; in this case, the ligation reaction can be carried out using a mixture of tag oligonucleotides, one for each of the possible alternative variants. Each tag would be labelled differently, for example, with a different fluophore, so that those that ligated could be recognised identifying the variant base (FIG. 3b).

Analysis of VNTR Lengths by Ligation to Anchored VNTRS

In this application "tag" oligonucleotides are ligated to sets of tethered oligonucleotides after hybridisation of the target, which acts as a template to bring the tags and the tethered oligonucleotides together.

Figure 4A:
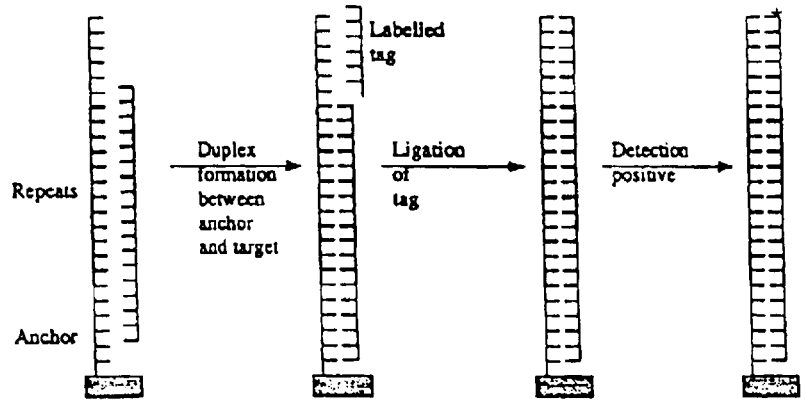
FIG. 4A shows analysis of variable numbered tandem repeats by ligation of tag to allelic variants.
Figure 4A:
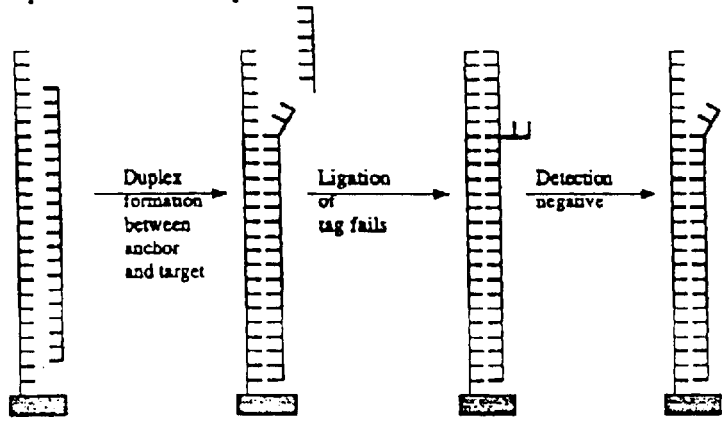
Figure 4A:
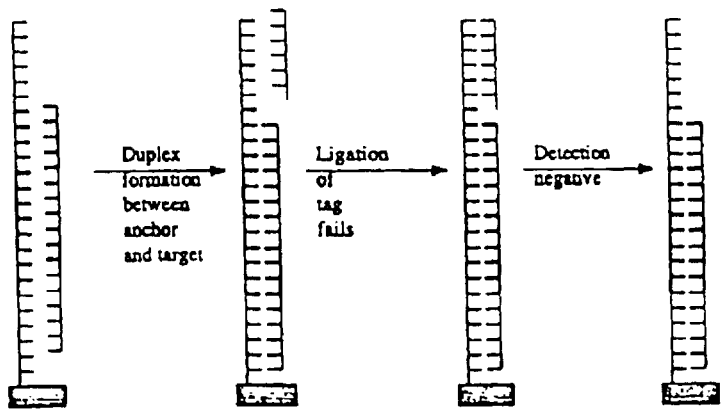

In FIG. 4a, the tethered oligonucleotides comprise three parts, an "anchor" sequence which is common to all members of a VNTR set, which is attached to the solid support and which hybridises to a sequence flanking the variable region, a variable number of the repeated sequence unit, and a distal sequence. Each allele, represented by a different number of repeats, is located on a different solid support or at a different location on the same solid surface. Hybridisation of the target sequence will produce a series of duplexes, the structures of which depend on the number of units that the target contains. If the number matches the number in a tethered oligonucleotide, the target will meet the end of a tag when the tag is hybridised to the distal sequence of the tethered oligonucleotide. If the number is greater or smaller, there will be a gap in the duplex which reduces or prevents ligation of the tag.

Figure 4B:
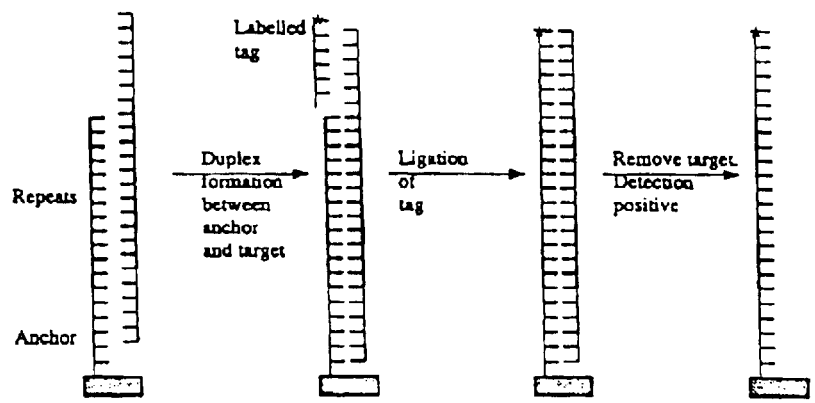
FIG. 4B shows analysis of variable number tandem repeats by ligation of tag to allelic variants.
Figure 4B:
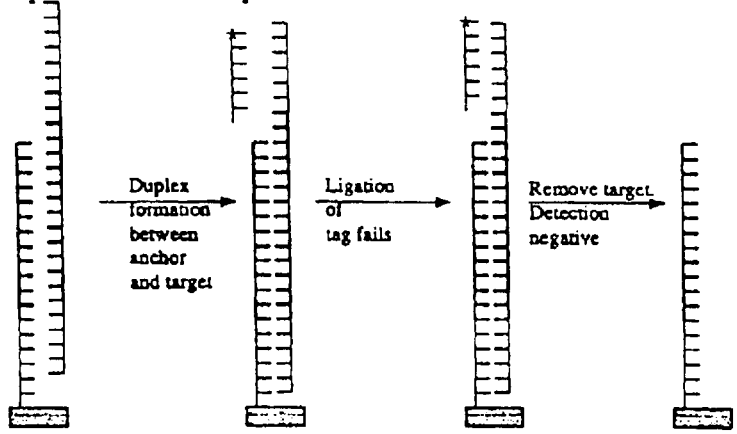
Figure 4B:
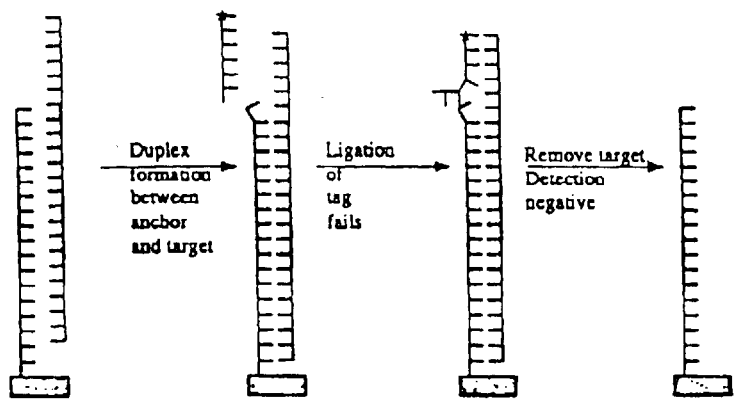

In FIG. 4b, the tethered oligonucleotides comprise two parts: an "anchor" sequence which is common to all members of a VNTR set and which hybridises to a sequence flanking the repeated region, and a variable number of the repeated sequence unit. Each allele, represented by a different number of repeats, is located on a different solid support, or at a different location on the same solid surface. Hybridisation of the target sequence will produce a series of duplexes, the structures of which depend on the number of repeat units that the target contains (FIG. 4b). If the number matches the number in a tethered oligonucleotide, the latter will meet the end of the tag when the tag is hybridised to its complement in the target sequence, and form a substrate for ligation of the tag. If the number is greater or smaller, there will be a gap in the duplex which reduces or prevents ligation of the tag.

Analysis of VNTR Lengths by Chain Extension

Figure 5:
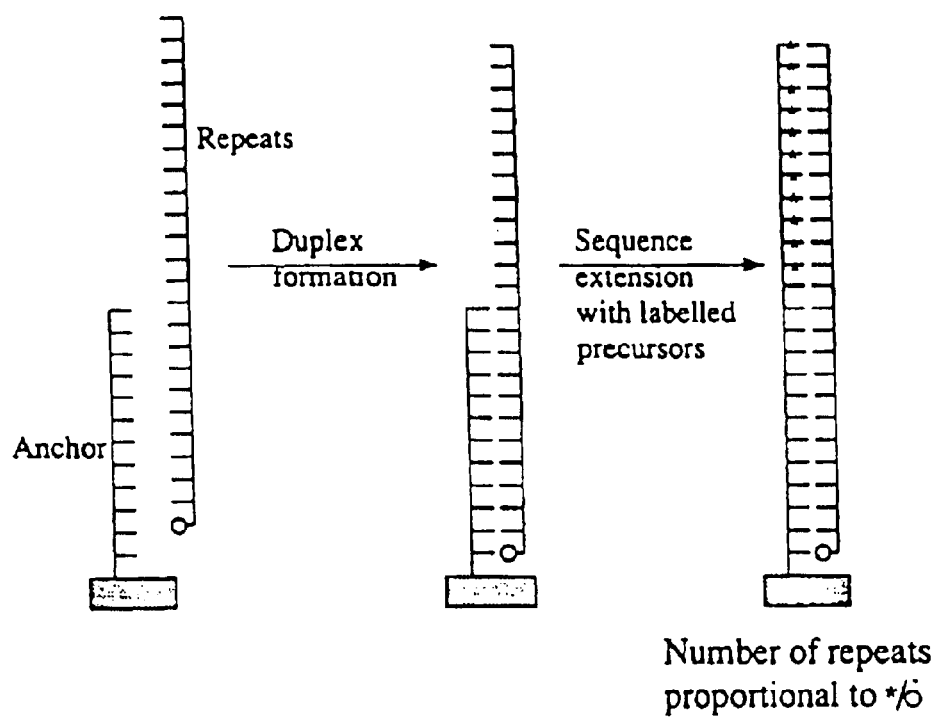
FIG. 5 shows measurement of variable number tandem repeats by labelled chain extension.

The number of repeat units in a VNTR may vary within small limits, and in these circumstances, the method of analysis described above, using a ligase, will be appropriate; in other cases, for example the trinucleotide repeats associated with a number of human inherited disorders, the variation may be too large to analyse in this way. For a number of triplet repeats, the variation can be from around 10–50 in the normal chromosome to more than a thousand in the affected individual (Table 1). It is probably unrealistic to measure such large numbers of repeats using the ligase reaction. In these cases, where the difference between the normal and the mutant allele is large, an alternative is to measure approximately the number of repeat units using labelled precursors with a polymerising enzyme. The enzyme may be either a polymerase, such as DNA dependent DNA polymerase, or a ligase. In the former case, the oligonucleotides have to be tethered at their 5'ends to satisfy the requirement for enzymatic extension by the polymerase. The solid support carries an oligonucleotide anchor complementary to a sequence flanking the repeat unit; for example, the sequence can be that of one of the primers used to amplify the test sequence by the PCR. After hybridisation of the test sequence to the anchor, the repeat insert may be copied by a polymerase or a ligase (FIG. 5) incorporating a labelled precursor. The amount of label incorporated is proportional to the number of repeat units. Incomplete hybridisation of the target to the anchor sequence would give a deceptively low measure of the repeat number. This problem can be overcome by standardising the measurement in one of several possible ways. For example, if the target sequence itself is labelled as shown in FIG. 5, the final measurement will be a ratio of two labels: the target and the incorporated precursor.

Alternatively, in the case of a triplet repeat, incorporation will end at the point in the sequence where the missing precursor base is needed for further extension; where a ligase had been used to polymerise monomers of the basic repeat unit, this will also end at the end of the VNTR insert. At this point a labelled "capping" sequence can be added by ligation. In such cases, the measurement will be the ratio of cap to polymer labels.

Analysis of VNTR Lengths by Combining Ligation and Chain Extension

Figure 6:
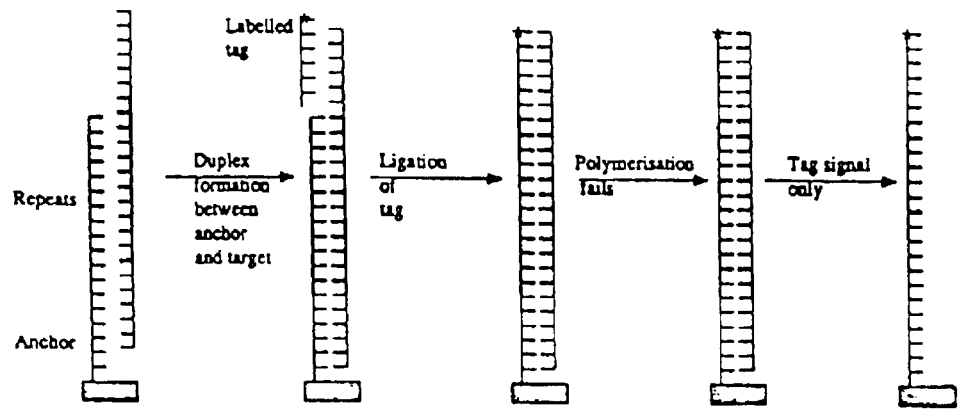
FIG. 6 shows analysis of variable number tandem repeats by ligation of tag followed by chain extension.
Figure 6:
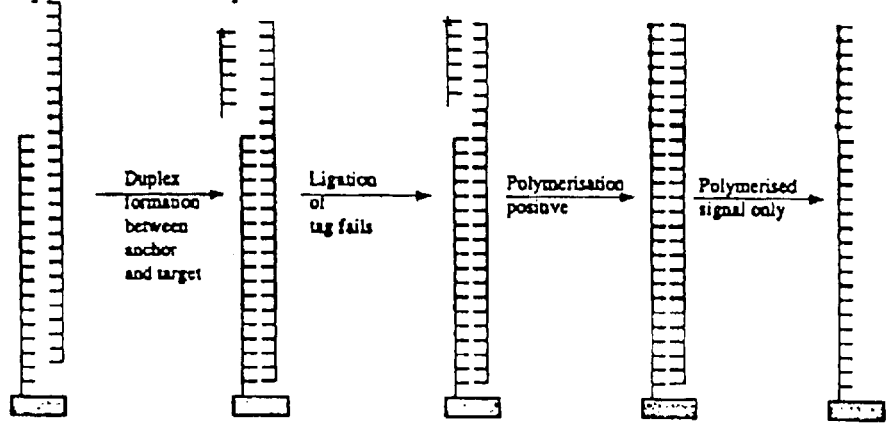
Figure 6:
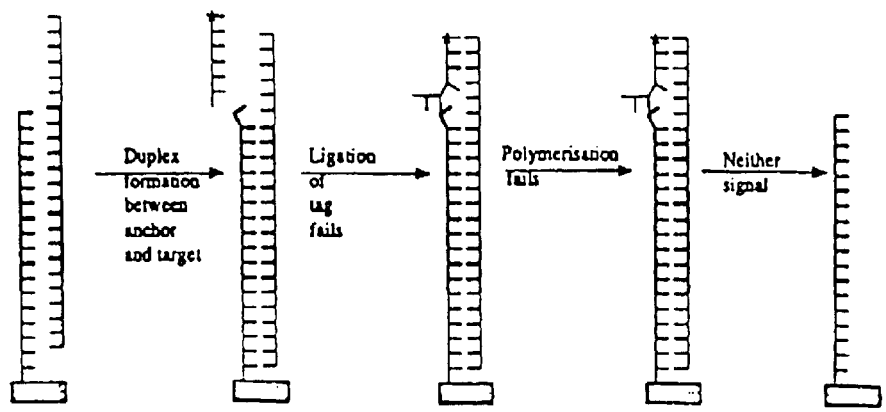

A more powerful way of analysing VNTRs which may vary in length over a wide range, would be to test first for ligation to a labelled tag oligonucleotide; this would give the results already described for targets with different lengths of repeats: a negative result where the VNTR lengths were longer or shorter in the target than in the tethered oligonucleotides, and positive results where they were the same. Following ligation, which we have shown can be made to go to completion, the different length classes will behave differently as substrates for DNA polymerase. Those targets in which the repeat number is less than that of the tethered probe will not act as substrates (FIG. 6c). Targets which have the same number of repeats as the probes will not be elongated by polymerase, because the ligated tag will block extension (FIG. 6a). The only cases where extension will occur are those for which the targets are longer than the probes (FIG. 6b). If the analysis is done on an array of probes with different numbers of inserts up to a certain limit, there will be a clear indication of the number of repeats in the targets from the ligation results provided they are within the range of sizes represented in the array of probes. If, within the targets, there is one which is longer than this range, it will show up in the polymerase analysis. This test will be especially useful for the triplet repeats associated with the so-called "dynamic mutations", for example, that which is found in the fragile×mutation, where the size range varies from ca. 10–1000. It would be difficult to accommodate all of these size classes on a single array.

Experimental Support for the Claims

Properties of DNA Polymerases and Ligases

Most DNA polymerases, reverse transcriptases, some DNA dependent RNA polymerases and ligases can use as substrates one or more oligonucleotides which are bound to a long DNA strand through Watson-Crick base pairing. In the case of polymerases, an oligonucleotide is used as a primer to which the first base in the growing chain is added. In the case of ligases, two oligonucleotides are joined provided that both are paired to the DNA strand and perfectly matched in the base pairs at or close to the junction point. It is these properties that make the enzymes useful for the detection of DNA sequence variation; in particular, the requirement for specific base pairing at the site of extension or joining complements the sequence discrimination that is already provided by the Watson-Crick pairing between the oligonucleotide and the target sequence that is needed to form a stable duplex. Thus, it has been found that discrimination by hybridisation alone is most sensitive if the variant base(s) is (are) close to the middle of the oligonucleotide. By contrast, for the enzymes, discrimination is highest if the variant mismatching bases are close to the end where the extension or join takes place. Together, hybridisation under stringent conditions and enzymatic extension or joining provide greater discrimination than either alone, and several methods have been developed to exploit this combination in systems for genetic analysis [references in cotton, 1993]. The hybridisation and the enzyme reaction are normally carried out in solution, following which the product is captured on a solid support, or separated by gel electrophoresis for detection and/or measurement.

In one embodiment, the invention described here employs oligonucleotides coupled to a solid surface, so that the advantages of working in mixed phase are brought to all steps: hybridisation, enzymatic extension or joining, and detection. This provides great sensitivity and convenience. As many different oligonucleotides can be bound to one surface in an array, it enables many different sequences to be analysed together, in a single reaction; this also ensures that all reactions are carried out under identical conditions, making comparisons more reliable.

Support-bound Oligonucleotides

Two different methods have been developed for making oligonucleotides bound to a solid support: they can be synthesised in situ, or presynthesised and attached to the support. In either case, it is possible to use the support-bound oligonucleotides in a hybridisation reaction with oligonucleotides in the liquid phase to form duplexes; the excess of oligonucleotide in solution can then be washed away. Hybridisation can be carried out under stringent conditions, so that only well-matched duplexes are stable. When enzymes are to be used, the chemical orientation of the oligonucleotide is important; polymerases add bases to the 3'end of the chain; ligases join oligonucleotides which are phosphorylated at the 5'end to those with a 3'-OH group. Oligonucleotides tethered to the solid substrate through either end can be made in situ by using the appropriate phosphoramidite precursors [references in Beaucage and Iyer, 1992]; or presynthesised oligonucleotides can be fixed through appropriate groups at either end. We will demonstrate that oligonucleotides can be phosphorylated at the 5' end in situ using ATP and polynucleotide kinase, or they may be phosphorylated chemically [Horn and Urdea, 1986].

Tethered Oligonucleotides as Substrates for DNA Modifying Enzymes

The applications envisaged here require that the oligonucleotides tethered to the solid substrate can take part in reactions catalysed by DNA polymerases and ligases.

DNA polymerase

The M13 sequencing primer-5'-GTAAAACGACGGCCAGT-3'-(SEQ ID No. 1) attached to aminated polypropylene through its 5' end was synthesised as described. A solution of M13 DNA (single-strand, replicative form, 0.1 $\mu$l, 200 ng/$\mu$l) was applied in two small spots to the surface of the derivatised polypropylene. A solution containing three non-radioactive deoxyribonucleotide triphosphates, dATP, dGTP, TTP (10 $\mu$mol each), $\alpha^{32}$P-dCTP (10 $\mu$Ci), Taq DNA polymerase and appropriate salts, was applied over a large area of the polypropylene, including the area where the M13 DNA had been spotted. The polypropylene as incubated at 37° C. for 1 hr in a vapour saturated chamber. It was then washed in 1% SDS at 100° C. for one minute, and exposed to a storage phosphor screen for one minute and scanned in a phosphorimager. The regions where the DNA had been applied showed a high level of radioactivity, against a low background where no DNA had been applied. This experiment shows that oligonucleotides tethered to a solid support can act as primers for DNA-dependent synthesis by DNA polymerase, as required for applications using this enzyme for mutation detection.

Experiments described below show that both polynucleotide kinase and DNA ligase can be used to modify oligonucleotides tethered to a solid support. There are several ways in which phosphorylated oligonucleotides and the ligase reaction can be used to detect sequence variation.

Methods for Making Arrays of Sequence Variants

1. Allele Specific Oligonucleotides for Point Mutations

For the preferred embodiment, it will be necessary to use oligonucleotides tethered to a solid support. The support may take the form of particles, for example, glass spheres, or magnetic beads. In this case the reactions could be carried out in tubes, or in the wells of a microtiter plate. Methods for both synthesising oligonucleotides and for attaching presynthesised oligonucleotides to these materials are known [Stahl et al., 1988]. Methods for making arrays of ASO's representing point mutations were described in patent application PCT/GB89/00460 and in Maskos and Southern (1993). We also demonstrated how oligonucleotides tethered to a solid support in an array could distinguish mutant from wild type alleles by molecular hybridisation.

For the present invention, the same methods could be used to create oligonucleotide arrays of ASOs, but in order that they can be used as substrates for the enzymes, they need to be modified; for ligation, it may be necessary to phosphorylate the 5' end; for extension by polymerase it will be necessary to attach to oligonucleotides to the solid substrate by their 5' ends.

2. Arrays for Scanning Regions for Mutations

It is often desirable to scan a relatively short region of a gene or genome for point mutations: for example, many different sites are mutated in the CFTR gene to give rise to cystic fibrosis; similarly, the p53 tumour suppressor gene can be mutated at many sites. The large numbers of oligonucleotides needed to examine all potential sites in the sequence can be made by efficient combinatorial methods [Southern et al., 1994]. A modification of the protocol could allow such arrays to be used in conjunction with enzymes to look for mutations at all sites in the target sequence.

3. VNTRs

The most commonly used VNTRs are repeats of very short units, typically mono to tetranucleotides. However, there is another class, the minisatellites, in which the repeat unit is somewhat longer, up to 20 or more nucleotides. The short repeats may be made using chemical synthesis; in the case of inserts with large numbers of repeat units, it would be more economical to use a synthetic route which used the repeat unit as a reactant, rather than building them up one base at a time; such methods have been used to make polynucleotides by chemical synthesis. An attractive alternative would be to build the repeat units by ligating the monomer units; they could be added stepwise, one unit at a time provided a method could be found to block one end to prevent polymerisation; for example the oligonucleotide building block may be terminated by a hydroxyl group, which is then phosphorylated after ligation so that the unit becomes an acceptor for the next one; the monomer may have a phosphate group protected by a cleavable group, such as a photocleavable group, which can be removed after ligation to allow a subsequent ligation [Pillai, 1980]. A second alternative, which would be especially favourable for longer units such the minisatellites, would be to attach either cloned or enzymatically amplified molecules to the solid support. For example, each variant sequence could be amplified by the PCR, using a biotinylated oligonucleotide for one of the primers. The strand starting with this group could then be attached to a streptavidin coated surface, and the other strand removed by melting [Stahl et al., 1988].

EXAMPLE 1

Demonstration of the Analysis of Length Polymorphism by Ligation to an Array of VNTRs An array of VNTRs was made as described in FIG. 4b, in which the anchor sequence was 5'-tgtagtggtgtgatcaaggc-3' (SEQ ID No. 2). The repeat unit was 5'-cttt-3'; stripes, ca 3 mm wide, of sequence variants of the form: Anchor-Repeat$_N$, with N=4–10, were made as stripes on the surface of a sheet of polypropylene. The synthesis was carried out using 3'-deoxyribophosphoramidites, this chemical orientation produces oligonucleotides tethered through their 3' ends to the polypropylene, and a free 5' hydroxyl group. To create a substrate for ligation, this OH group was phosphorylated by immersing a strip of the polypropylene (3 mm×18 mm), carrying the array of oligonucleotides, in 0.5 ml of a solution containing 4 mM ATP and 77.6 units of polynucleotide kinase with buffer and Mg$^{++}$ according to the supplier's instructions. The reaction was left for 6 hours at 37° C.; the strip was removed and immersed in boiling water to kill the polynucleotide kinase. The target sequences, which are complementary to elements of the array oligonucleotides and to the ligation tag, 5'-Anchor-Repeat$_{10}$-Tag and 5'-Anchor-Repeat$_5$-Tag were added to 0.5 ml of a solution, preheated to 95° C., containing the tag, 5'-gtggtcactaaagtttctgct-3', (SEQ ID No. 3), which had been labelled at its 5' end using polynucleotide kinase and $^{33}$P-gamma-ATP, thermal ligase (500 units), and buffer and salts according to the supplier's instructions. The polypropylene strip was immersed in the hot solution, which was then allowed to cool to 68° C., and left at this temperature for 16 hours. The polypropylene strip was removed and placed in 25% formamide at 95° C. for 5 minutes, rinsed in water at the same temperature, dried and exposed to a storage phosphor screen, from which an image of the radioactivity was collected. The results showed counts close to background over most of the array; counts on Anchor-Repeat$_5$ and Anchor-Repeat$_{10}$ were more than five times those over adjacent cells in the array. This experiment indicates that the ligase is able to distinguish length variants of the repeat sequence and gives optimum ligation only when the number of repeats in the target matches that in the allele specific oligonucleotide in the array. Thus, it should easily be possible to detect the two allelic variants in a heterozygote.

Ligation and/or polymerisation is possible if the oligonucleotide is tethered through the 5' end. The oligonucleotides can be synthesised in situ using deoxyribophosphoramidites with 3' dimethoxytrityl groups and 5' phosphoramidite (reverse phosphoramidites). It is unnecessary to phosphorylate the tethered polynucleotide for ligation assays since the phosphate needed for ligation is provided by the tag oligonucleotide.

EXAMPLE 2
Analysis of VNTR Lengths

An array of VNTR's was made as described in FIG. 4B, with the oligonucleotides anchored through their 5' ends. The repeat unit was 5' ttca and the anchoring sequence 5' cttatttccctca (SEQ ID No. 4). Stripes 6 mm wide of sequence variants of the form: Anchor-Repeat$_N$ where N=4–8 were made on the surface of a sheet of polypropylene using "reverse" phosphoramidite monomers.

Analysis by Ligation

A strip of the array (30 mm×2 mm) was immersed in a solution of 600 pmols of the target oligonucleotide 5' cacagactccatgg(tgaa)$_6$tgagggaaataag, (SEQ ID No. 5), 1.4 pmol of oligo 5' ccatggagtctgtg (SEQ ID No. 6) (labelled at its 5' end using polynucleotide kinase and $^{33}$P gamma ATP) and buffer and salts according to the suppliers instructions, the total volume being 293 µl. The solution was heated to 65° C. and 7 µl of Tth DNA ligase added. The reaction was then cooled to 37° C. and left at that temperature for 18 hrs. After removal from the reaction solution the strip was washed in T.E. buffer, blotted dry and exposed to a storage phosphor screen from which an image of the radioactivity was taken. The results showed that the target sequence ligated to the correct sequence with a higher yield than to the shorter and longer sequences in adjacent cells of the array.

EXAMPLE 3
Analysis by Ligation and Polymerisation

A strip of the array (30 mm×2 mm) from Example 2 was added to a solution of 200 pmols of the target oligonucleotide 5' cacagactccatgg(tgaa)$_6$tgagggaaataag, 200 pmol of oligo 5' ccatggagtctgtg (chemically phosphorylated at the 5' end) with buffer and salts according to the suppliers instructions, the total volume being 243 µl. The solution was heated to 85° C. and cooled to 37° C. over a period of 30 mins. 7 µl of Tth DNA ligase was added and the reaction mixture heated at 34° C. for 17 hrs. The strip was removed and added to a solution of 8 mM DTT, 3.3 pmol $^{32}$P alpha dTTP, 13 units sequenase version 2.0 and buffer and salts according to the suppliers instructions. The total volume was 250 µl. After heating at 37° C. for 3 hrs the strip was removed from the reaction solution, washed in TE buffer, blotted dry and exposed to a storage phosphor screen from which an image of the radioactivity was taken. The results showed counts equal to background over the area of the array where repeats were equal in length or greater than the repeat length of the target, with 20 times the signal in the areas where the repeat length of the array was shorter than the repeat length in the target.

EXAMPLE 4
Analysis by Polymerisation

Two types of polymerase analysis were carried out where reporter nucleotides were chosen, in one case to identify the correct repeat length, and in the other case to identify shorter repeat lengths. This is made possible when the repeat sequence comprises less than all four bases.

In the former case a base is chosen which is present in the repeat sequence and is different from the first base in the flanking sequence. In the latter case a base is chosen to be complementary to the first base in the flanking sequence which is absent from the repeat.

A strip of the array from Example 2 (30 mm×2 mm) was added to a solution of 500 pmols of the target oligonucleotide 5' cacagactccatgg(tgaa)$_6$tgagggaaataag in buffer and salts at a concentration 1.09 times the suppliers instructions, the total volume being 275 µl. The solution was heated to 75° C. for 5 minutes and cooled to 37° C. over a period of 25 mins. The solution was removed and added to 3.3 pmols $^{32}$P alpha dCTP, 5 µl 1M DTT. 13 units of Sequenase version 2.0 and water to give a final volume of 295 µl. This solution was added to the array and heated at 37° C. for 15 hrs 40 mins. The polypropylene strip was removed, washed in water and exposed to a storage phosphor screen. The results showed counts of 5 times more for the correct sequence than shorter sequences and twice for the correct sequence compared with longer repeats.

A similar strip of the array (30 mm×2 mm) was added to a solution of 500 pmols of the target oligonucleotide 5' cacagactccatgg(tgaa)$_6$tgagggaaataag in buffer and salts 1.09 times the suppliers instructions, the total volume being 275 µl. The solution was heated to 75° C. for 5 mins and cooled to 37° C. over a period of 25 mins. The solution was removed and added to 3.3 pmols $^{32}$P alpha dTTP, 5 µl 1M DTT, 13 units of Sequenase version 2.0 and water to give a final volume of 295 µl. This solution was added to the array and heated at 37° C. for 15 hrs 40 mins. The polypropylene strip was removed, washed in water and exposed to a storage phosphor screen. The results showed counts of 4.5 times more for the shorter array sequences than the correct and longer repeat lengths.

EXAMPLE 5
VNTR Analysis by Ligation

In an experiment similar to the one described in Example 1, an array was created using the human fes/fps locus sequence as a target. The anchor sequence 5' agagatgtagtct-cattctttcgccaggctgg 3' (SEQ ID No. 7) was the actual flanking sequence to the attt repeats of the fes/fps microsatellite (EMBL Accession No X06292 M14209 M14589) as it occurs in human genomic DNA. Using a target oligonucleotide representing the 10 repeat allele and ligating a $^{33}$P labelled 5' flanking sequence (5' g gag aca agg ata gca gtt c 3') (SEQ ID No. 8) and doing a similar experiment to that described above, the resulting radioactivity on the anchor-repeat$_{10}$ cell was over 10 fold that on adjacent cells in the array.

EXAMPLE 6
Demonstration of Stepwise Ligation of Oligonucleotides Bound to a Solid Support A primer oligodeoxynucleotide—5' PO$_4$ gta aaa cga cgg cca gt 3' (SEQ ID No. 9), attached to aminated polypropylene through its 3' end, was synthesised and phosphorylated as described. A small square (2 mm×2 mm) piece of this material was placed in standard ligation buffer, with template oligonucleotide 5' tcg ttt tac cgt cat gcg tcc tct ctc 3' (SEQ ID No. 10) (250 nM) and a protected ligator oligonucleotide 5' NB PO$_4$ cgc atg acg 3' (250 nM) and $^{33}$P labelled extender oligonucleotide 5' gag aga gga 3', where NB is a protecting group based on a photocleavable o-nitrobenzyl derivative. The NB protected phosphate of the ligator oligonucleotide had previously been shown to be unable to take part in the ligation reaction. The NB group had also been shown to be removable by uv light to leave a fully functional phosphate group. To this mixture was added thermus thermophilus DNA ligase (Advanced Biotechnologies) 25 u and the reaction incubated at room temperature for 6 hours. The mixture was then irradiated with uv light (20 minutes room temperature) and incubated for a further 12 hours. The polypropylene patch was then washed with 30% formamide at 95° C. for 5 minutes, and exposed to a storage phosphor screen for 24 hours and scanned in a phosphorimager. The patch showed a level of radioactivity 50 fold higher than a patch treated in a similar fashion but without addition of the central "ligator" oligonucleotide. In a similar experiment using a phosphorylated ligator oligonucleotide a similar amount of radioactive extender oligonucleotide became covalently attached to a third polypropylene/oligonucleotide primer square.

EXAMPLE 7
Demonstration of Point Mutation Analysis by Ligation to Allele Specific Oligonucleotides Attached to Solid Supports Four tethered ASOs 5' (gca or t)ag aga gga 3', differing only at their 5' base, were synthesised as described above, with the 3' end attached to aminated polypropylene. Phosphorylation was carried out as described and four squares of polypropylene carrying each ASO were placed in standard ligation buffer along with complementary target oligonucleotide 5' tcc tct ctc cgt cat gcg tat cgt tca at 3' (SEQ ID No. 11) (250 nM). After addition of $^{33}$P labelled ligator oligonucleotide 5' cgc atg acg 3' (10 nM) and thermus thermophilus DNA ligase (100 u), the mixture was incubated at 37° C. for 18 hours. The ASO which was fully complementary to the target oligonucleotide was found to have acquired 100-fold greater radioactivity through ligation of the labelled ligator than the non-complementary ASOs.

EXAMPLE 8
Demonstration of DNA Ligation Specificity

In a model experiment to assess the specificity of TTh DNA ligase, ligator and extender deoxyoligonucleotides were ligated together by means of hybridisation to an oligonucleotide template and ligation by DNA ligase.

Template oligonucleotide 5' tcc tct ctc cgt cat gcg tat cgt tca at 3' (SEQ ID No. 12) (250 nM), phosphorylated, $^{33}$P labelled, extender oligonucleotide 5' PO$_4$gag aga gga 3' (10 nM) and ligator sequence 5' gca gta cg 3' (250 nM) were mixed together in standard ligation buffer with DNA ligase 25 u. This mixture was incubated at 35° C. Samples of this mixture were removed and the reaction stopped by addition of formamide at 15, 30, 60, 120, and 240 minutes. The ligated and unligated products were separated by 20% denaturing polyacrylamide gel electrophoresis. The gel was exposed to a phosphor screen for 18 hours and scanned by a phosphorimager. The relative proportions of ligated to unligated products of the reaction were then measured. 50% of the extender sequence had been ligated to the ligator sequence in 30 minutes. By comparison in a similar experiment with ligator 5' gca tga ag 3' after 30 minutes only 1% of the extender sequence had become ligated.

Other polymerases and ligases such as Taq polymerase, Thermosequenase, T4 DNA ligase and E.Coli DNA ligase have also been shown to be useful in experiments similar to those described above.

REFERENCES

1. Beaucage, S. L. and Iyer, R. P. (1992). Advances in the synthesis of oligonucleotides by the phosphoramidite approach. Tetrahedron 48: 2223–2311.
2. Conner, B. J., Reyes, A. A., Morin, C., Itakura, K., Teplitz, R. L., and Wallace, R. B. (1983). Detection of sickle cell $\beta^s$ globin allele by hybridization with synthetic oligonucleotides. Proc. Natl. Acad. Sci. USA 80: 278–282.
3. Cooper, D. N., and Krawczak, M. (1989). The mutational spectrum of single base-pair substitutions causing human genetic disease: patterns and predictions. Hum. Genet. 85: 55–74.
4. Cotton, R G, (1993) Current methods of mutation detection. Mutation Research 285: 125–144.
5. Horn, T., and Urdea, M. (1986) Chemical phosphorylation of oligonucleotides. Tetrahedron Letters 27: 4705.
6. Khrapko, K. R., Lysov, Yu. P., Khorlyn, A. A., Shick, V. V., Florentiev, V. L., and Mirzabekov. (1989). An oligonucleotide hybridization approach to DNA sequencing. FEBS Lett. 256: 118–122.
7. Krawczak M. and Schmidtke, J. (1994). DNA fingerprinting. BIOS Scientific Publishers.
8. Maskos, U., and Southern, E. M., (1993) A novel method for the analysis of multiple sequence variants by hybridisation to oligonucleotides. Nucleic Acids Research, 21: 2267–2268.
9. Pillai, V. N. R.(1980). Photoremovable protecting groups in organic chemistry Synthesis 39: 1–26.
10. Southern, E. M. (1988). Analyzing Polynucleotide Sequences. International Patent Application PCT/GB89/00460.
11. Southern, E. M., Maskos, U. and Elder, J. K. (1992). Analysis of Nucleic Acid Sequences by Hybridization to Arrays of Oligonucleotides: Evaluation using Experimental Models. Genomics 12:1008–1017.
12. Southern, E. M., Case-Green, Elder, J. K. Johnson, M., Mir, K. U., Wang, L., and Williams, J. C. (1994). Arrays of complementary oligonucleotides for analysing the hybridisation behaviour of nucleic acids. Nucleic Acids Res. 22: 1368–1373.
13. Stahl, S., Hultman, T., Olsson, A., Moks, T. D and, Uhlen, M. (1988) Solid phase DNA sequencing using the biotin-avidin system. Nucleic Acids Res. 16: 3025–38.
14. Veerle, A. M. C. S., Moerkerk, P. T. M. M., Murtagh, J. J., Jr., Thunnissen, F. B. J. M (1994) A rapid reliable method for detection of known point mutations: Point-EXACCT. Nucleic Acids Research 22: 4840–4841.
15. Virnekas, B., Liring, G., Pluckthon, K., Schneider, C., Wellhofer, G. and Moroney, S. E. (1994) Trinucleotide phosphoramidites: ideal reagents for the synthesis of mixed oligonucleotides for random mutagenesis. Nucleic Acids Research 22: 5600–5607.
16. Willems, P. J. (1994) Dynamic mutations hit double figures. Nature Genetics 8: 213–216.

| DNA sequences of triplet repeats | | | | | |
|---|---|---|---|---|---|
| Condition | Repeat | Normal | Preexpansion | Expanded | Reference |
| FRAXA | CGG/CCG | 10–50 | 38–50 | 200–1000 | Verkerk e tal. 1991 |
| FRAXE | CGG/CCG | | | 200–1000 | Knight et al. 1993 |
| FRAXF | GCC/CGG | 6–18 | ? | 300–500 | Parrish et al. 1994 |
| FRAX16A | CGG/CCG | | | 1000–2000 | Nancarrow et al. 1994 |
| SBMA | CAG | 11–31 | ? | 40–62 | Tilley et al. 1994 |
| Huntington | CAG | 11–34 | 30–34 | 42–100 | Huntington group 1993 |
| SCA1 | CAG | 25–36 | ? | 43–81 | Orr et al. 1993 |
| DRPLA/HRS | CAG | | | ≦100 | Burke et al. 1994 |
| Machado-Joseph | CAG/CTG | ~26 | ? | 68–79 | Kawaguchi et al. 1994 |

What is claimed is:

1. An array of oligonucleotide probes, for analysing a polynucleotide target containing a variable sequence, in which each component oligonucleotide (i) comprises a sequence complementary to the target including an expected variant of the target, (ii) has a free 3'-OH group and/or a free 5'-phosphate, and (iii) is tethered to a solid support in an orientation which (a) permits duplex formation with the target, and (b) permits ligation or chain extension only when the sequence of the oligonucleotide matches the variable sequence of the target.

2. The array of claim 1, wherein the probes are tethered by a covalent linkage.

3. The array of claim 1, wherein the probes are tethered through a 5' or 3' nucleotide.

4. The array of claim 1, wherein the probes are tethered at spaced locations on a derivatised glass surface or on the surface of a silicon microchip or on propylene.

5. The array of claim 1, wherein the probes are tethered to individual beads.

6. The array of claim 1, wherein the probes are synthesised in situ.

7. The array of claim 1, wherein the probes are pre-synthesised.

8. An array of oligonucleotide probes, for analysing a polynucleotide target containing a variable number tandem repeat sequence, in which each component oligonucleotide is tethered to a solid support and (i) comprises a sequence complementary to a part of the target immediately adjacent the repeat sequence, (ii) has a free 3'-OH group and/or a free 5'-phosphate, (iii) comprises a sequence complementary to the repeat sequence of the target and containing a number of repeats expected in the target, and (iv) is configured in a way that (a) permits duplex formation with the target, and (b) permits ligation or chain extension only when the number of repeats in the oligonucleotide equals or is less than the number of repeats in the target.

9. The array of claim 8, wherein each component oligonucleotide (iv) is configured in a way that (b) permits chain extension: by ligation only when the number of repeats in the oligonucleotide equals the number of repeats in the target; or by polymerisation only when the number of repeats in the oligonucleotide is less than the number of repeats in the target.

10. The array of claim 8, wherein the probes are tethered by a covalent linkage.

11. The array of claim 8, wherein the probes are tethered through a 5' or 3' nucleotide.

12. The array of claim 8, wherein the probes are tethered at spaced locations on a derivatised glass surface or on the surface of a silicon microchip or on propylene.

13. The array of claim 8, wherein the probes are tethered to individual beads.

14. The array of claim 8, wherein the probes are synthesised in situ.

15. The array of claim 8, wherein the probes are pre-synthesised.

* * * * *

SEQUENCE LISTING

<160> NUMBER OF SEQ ID NOS: 12

<210> SEQ ID NO 1
<211> LENGTH: 17
<212> TYPE: DNA
<213> ORGANISM: Unknown
<220> FEATURE:
<223> OTHER INFORMATION: Description of Unknown Organism:synthetic - other dna

<400> SEQUENCE: 1
gtaaaacgac ggccagt                                                    17

<210> SEQ ID NO 2
<211> LENGTH: 20
<212> TYPE: DNA
<213> ORGANISM: Unknown
<220> FEATURE:
<223> OTHER INFORMATION: Description of Unknown Organism:synthetic - other dna

<400> SEQUENCE: 2
tgtagtggtg tgatcaaggc                                                 20

<210> SEQ ID NO 3
<211> LENGTH: 21
<212> TYPE: DNA
<213> ORGANISM: Unknown
<220> FEATURE:
<223> OTHER INFORMATION: Description of Unknown Organism:synthetic - other dna

<400> SEQUENCE: 3
gtggtcacta aagtttctgc t                                               21

<210> SEQ ID NO 4
<211> LENGTH: 13
<212> TYPE: DNA
<213> ORGANISM: Unknown
<220> FEATURE:
<223> OTHER INFORMATION: Description of Unknown Organism:synthetic - other dna

```
<400> SEQUENCE: 4
cttatttccc tca                                                    13

<210> SEQ ID NO 5
<211> LENGTH: 51
<212> TYPE: DNA
<213> ORGANISM: Unknown
<220> FEATURE:
<223> OTHER INFORMATION: Description of Unknown Organism:synthetic -
      other dna

<400> SEQUENCE: 5
cacagactcc atggtgaatg aatgaatgaa tgaatgaatg agggaaataa g           51

<210> SEQ ID NO 6
<211> LENGTH: 14
<212> TYPE: DNA
<213> ORGANISM: Unknown
<220> FEATURE:
<223> OTHER INFORMATION: Description of Unknown Organism:synthetic -
      other dna

<400> SEQUENCE: 6
ccatggagtc tgtg                                                   14

<210> SEQ ID NO 7
<211> LENGTH: 32
<212> TYPE: DNA
<213> ORGANISM: Unknown
<220> FEATURE:
<223> OTHER INFORMATION: Description of Unknown Organism:synthetic -
      other dna

<400> SEQUENCE: 7
agagatgtag tctcattctt tcgccaggct gg                               32

<210> SEQ ID NO 8
<211> LENGTH: 20
<212> TYPE: DNA
<213> ORGANISM: Unknown
<220> FEATURE:
<223> OTHER INFORMATION: Description of Unknown Organism:snythetic -
      other dna

<400> SEQUENCE: 8
ggagacaagg atagcagttc                                             20

<210> SEQ ID NO 9
<211> LENGTH: 17
<212> TYPE: DNA
<213> ORGANISM: Unknown
<220> FEATURE:
<223> OTHER INFORMATION: Description of Unknown Organism:synthetic -
      other dna

<400> SEQUENCE: 9
gtaaaacgac ggccagt                                                17

<210> SEQ ID NO 10
<211> LENGTH: 27
<212> TYPE: DNA
<213> ORGANISM: Unknown
<220> FEATURE:
<223> OTHER INFORMATION: Description of Unknown Organism:synthetic -
      other dna

<400> SEQUENCE: 10
```

```
tcgttttacc gtcatgcgtc ctctctc                                              27

<210> SEQ ID NO 11
<211> LENGTH: 27
<212> TYPE: DNA
<213> ORGANISM: Unknown
<220> FEATURE:
<223> OTHER INFORMATION: Description of Unknown Organism:synthetic -
      other dna

<400> SEQUENCE: 11
tcctctctcc gtcatgcgta tcgttca                                              27

<210> SEQ ID NO 12
<211> LENGTH: 27
<212> TYPE: DNA
<213> ORGANISM: Unknown
<220> FEATURE:
<223> OTHER INFORMATION: Description of Unknown Organism:synthetic -
      other dna

<400> SEQUENCE: 12
tcctctctcc gtcatgcgta tcgttca                                              27
```